United States Patent [19]
Virnig et al.

[11] Patent Number: 6,107,523
[45] Date of Patent: Aug. 22, 2000

[54] BETA-DIKETONES FOR THE EXTRACTION OF COPPER FROM AQUEOUS AMMONIACAL SOLUTIONS

[75] Inventors: Michael J. Virnig; Gary A. Kordosky, both of Tucson, Ariz.; Sang I. Kang, Ft. Washington, Pa.; Kevin V. Martin, Linden, N.J.; Phillip L. Mattison, North Wales, Pa.

[73] Assignee: Henkel Corporation, Gulph Mills, Pa.

[21] Appl. No.: 08/992,023

[22] Filed: Dec. 17, 1997

Related U.S. Application Data

[63] Continuation-in-part of application No. 08/780,759, Jan. 8, 1997, abandoned.

[51] Int. Cl.$^7$ .................................................. C07C 45/77
[52] U.S. Cl. ......................... 568/412; 568/331; 568/335; 423/24
[58] Field of Search ............................... 423/24; 568/331, 568/335, 412

[56] References Cited

U.S. PATENT DOCUMENTS

| | | | |
|---|---|---|---|
| 2,727,818 | 12/1955 | Kenny et al. | 75/103 |
| 3,985,553 | 10/1976 | Kunda et al. | 75/103 |
| 4,022,866 | 5/1977 | Kuhn et al. | 423/26 |
| 4,065,502 | 12/1977 | MacKay et al. | 260/590 |
| 4,175,012 | 11/1979 | MacKay et al. | 204/108 |
| 4,350,661 | 9/1982 | Davis et al. | 422/98 |
| 4,563,256 | 1/1986 | Sudderth et al. | 204/108 |

FOREIGN PATENT DOCUMENTS

| | | |
|---|---|---|
| 668358 | 8/1996 | Australia . |
| 0 036 401 | 9/1981 | European Pat. Off. . |
| 2 355 064 | 1/1976 | France . |
| WO93/04208 | 3/1993 | WIPO . |

OTHER PUBLICATIONS

"Physical and Chemical Separations via the Arbiter Process", Kuhn & Arbiter, International Mining Congress, Apr., 1975, Cagliari, Italy, pp. 831–847.

"Anaconda's Arbiter Process for Copper", Kuhn & Arbiter, CIM Bulletin, Feb., 1974.

*Primary Examiner*—Gary Geist
*Assistant Examiner*—S. Padmanabhan
*Attorney, Agent, or Firm*—Ernest G. Szoke; Wayne C. Jaeschke; Patrick J. Span

[57] ABSTRACT

Novel modified and improved beta-diketones and their use in the extraction of copper from aqueous ammoniacal solutions containing copper values, resulting from commercial processes, including, but not limited to, leaching of copper containing ores, such as sulfidic ores, or concentrates resulting from flotation of such sulfidic ores. The novel diketones are those highly sterically hindered, which may be represented by the formula I or II:

$$R_2-\underset{\underset{R_3}{|}}{\overset{\overset{R_1}{|}}{C}}-\overset{\overset{O}{\|}}{C}-\underset{\underset{R_4}{|}}{CH}-\overset{\overset{O}{\|}}{C}-\underset{\underset{R_5}{|}}{\overset{\overset{R_7}{|}}{C}}-R_6 \quad [\text{I}]$$

$$R-\overset{\overset{O}{\|}}{C}-\underset{\underset{R''}{|}}{CH}-\overset{\overset{O}{\|}}{C}-\underset{\underset{R'''}{|}}{\overset{\overset{R''''}{|}}{C}}-R' \quad [\text{II}]$$

The preferred beta-diketones of Formula [II] are selected from the group consisting of neo-alkyl beta-diketones, such as, 1-phenyl-3-neoalkyl-1,3 propanedione in which the neoalkyl group is selected from neohexyl, neoheptyl, neooctyl, neononyl, or neodecyl.

28 Claims, No Drawings

BETA-DIKETONES FOR THE EXTRACTION OF COPPER FROM AQUEOUS AMMONIACAL SOLUTIONS

This application is a continuation-in-part application of U.S. Ser. No. 08/780,759 filed Jan. 8, 1997 the entire disclosure of which is hereby incorporated herein by reference.

BACKGROUND OF THE INVENTION

1. Field of the Invention

This invention relates to new, improved beta-diketones and their use in the extraction of copper from aqueous ammoniacal solutions containing copper values, resulting from commercial processes, including, but not limited to, leaching of copper containing ores, such as sulfidic ores, or concentrates resulting from flotation of such sulfidic ores.

2. Statement of Related Art

Practice in the recovery of copper from its sulfidic ores involves subjecting the ores to a froth flotation operation to produce a concentrate of the valuable metal sulfides and to reject the flotation tailings of valueless sulfides, silicates, aluminates and the like. One of such concentrates provided is a chalcocite concentrate containing chalcocite and covellite.

In U.S. Pat. No. 4,022,866 to Kuhn and Arbiter, and in their subsequent paper, "Physical and Chemical Separations via the Arbiter process" 11th International Mining Congress, April, 1975, Cagliari, Italy; proc.-Int. Miner. Process. Congress., paper 30; pp.831–847; there is described the leaching of copper sulfide concentrates with ammonia/ammonium sulfate and oxygen whereby the sulfate, and the dissolved copper may then be recovered by solvent extraction. The solvent extraction reagents are described in the patent only generally as those which preferentially load copper from alkaline solutions. In the paper, which describes the Arbiter process, the focus is on complete or nearly complete leaching of the concentrate. Another Kuhn and Arbiter paper, "Anaconda's Arbiter Process for Copper", Hydrometallurgy, CIM Bulletin, February, 1974, contains similar description.

U.S. Pat. No. 4,563,256 describes a solvent extraction process for the recovery of zinc values from ammoniacal solutions, which may also contain copper values, using or employing various oxime extractants.

U.S. Pat. No. 2,727,818 describes a method of leaching copper sulfide materials with ammoniacal leach solutions. No solvent extraction is discussed.

U.S. Pat. Nos. 4,065,502 and 4,175,012 describes beta-diketones which may be employed as metal extractants in a liquid—liquid ion exchange process for recovery of metals, such as nickel or copper, from aqueous solutions containing the metal values, including aqueous ammoniacal solutions.

U.S. Pat. No. 4,350,661 describes the extraction of copper from ammoniacal aqueous solutions by a process of extraction first with a beta-diketone followed by a second extraction with an oxime. Alternatively, there is described the use of a mixture of diketone and oxime wherein the extractant reagent comprises about 5–30 percent by volume of the strong reagent (oxime) and 10–60 percent by volume of the weak reagent (beta diketone).

In commonly assigned, application, U.S. Ser. No. 07/745, 028, Australian Patent No. 668358, issued Aug. 20, 1996, corresponding thereto, there is described a partial leaching of a chalcocite concentrate, to provide an aqueous ammoniacal leach solution containing copper values, and the use of high copper transfer, low ammonia loading extraction reagents such as a beta-diketone. An oxime extractant is also disclosed alone or with the diketone.

DESCRIPTION OF THE INVENTION

In this description, except in the operating examples or where explicitly otherwise indicated, all numbers describing amounts of ingredients or reaction conditions are to be understood as modified by the word "about".

It was found that when contacted with an ammoniacal solution obtained by leaching a copper sulfide concentrate with ammonia/ammonium sulfate, a preferred diketone extractant reagent, 1-phenyl-3-isoheptyl-1,3-propanedione, will extract the copper but upon repetitive use the copper may become more difficult to strip. It is believed that the problem may arise from a synergistic interaction of surfactant type materials introduced into the organic phase through a leach liquor, with a ketimine that is formed by reaction of ammonia with the beta-diketone. Whatever the mechanism, the observation is that the kinetics of copper stripping becomes slower, so that for a given contact time of loaded organic with aqueous strip solution, the organic becomes less completely stripped. This presents two disadvantages when the stripped organic is recycled to extraction; there is less capacity to extract more copper, and the driving force for copper extraction is reduced, leading to less complete extraction.

Particularly when a diketone such as 1-phenyl-3-isoheptyl-1.3-propanedione is contacted with ammoniacal copper solutions having a relatively high pH, there tends to be a quantity of ammonia coextracted with the copper, typically about 5 mole percent relative to extracted copper. Even though this is a relatively small fraction, it constitutes a significant cost of operation. If the ammonia is allowed to remain on the loaded organic and proceed to stripping, the ammonia will consume acid and report to the stripping solution as the ammonium salt, where it will tend to accumulate with time as the stripping solution is recycled. It is generally preferable to first wash the ammonia from the loaded organic by contacting it with a dilute aqueous acid solution. Acid is still consumed in this step, but the ammonium salt is produced in a solution separate from the stripping solution. Thus coextracted ammonia represents a cost both of the lost ammonia as well as of the acid required to remove it from the loaded organic. It would be desirable to have an extractant for copper from aqueous ammonia that not only would be stable and resistant to ketimine formation, but also retained fast stripping kinetics and coextracted less ammonia when loaded with copper.

It has now been discovered that the use of a sterically hindered beta-diketone, will provide a very efficient and improved process for the recovery of copper in that a significant improvement in the stability of strip kinetics will be achieved. It is believed that the steric hindrance around the beta-diketone functionality results in more stability to use conditions, minimizing, if not eliminating, ketimine formation. It has also been discovered that the use of diketones having very high steric hindrance will provide a further improved process in which strip kinetics remain rapid, and substantially reduced coextraction of ammonia occurs during loading with copper.

By "highly sterically hindered diketone" as employed herein is meant that the diketone is highly sterically hindered where the three carbons attached to the carbonyl carbons of the diketone can together bear no more than three hydrogens when none of the three carbons is a part of a phenyl ring and no more than two hydrogens when one of the two carbons is part of a phenyl ring. It is also required that the carbon atom between the two carbonyl carbons must bear at least one hydrogen. Particularly preferred are those diketones in which one of the two carbons alpha to the carbonyl carbons is part of an aryl or alkaryl ring, and the other alpha carbon is substituted with three alkyl groups.

While the present invention is particularly useful in applications where ammoniacal leach solutions are encountered in the treatment of copper containing sulfidic ores, the present invention is applicable or useful in the extraction of copper from any aqueous ammoniacal solution containing copper values regardless of its source.

In its general application accordingly the present invention is an improvement in the process of extraction and recovery of copper from aqueous ammoniacal solutions in a process comprising:

(1) contacting a copper pregnant aqueous ammoniacal solution containing copper values with a water insoluble beta-diketone copper extractant dissolved in a water immiscible organic solvent to extract copper values from said aqueous ammoniacal solution into said organic solution thereby forming a copper pregnant organic phase and a copper depleted aqueous phase;
(2) separating said aqueous phase and said organic phase;
(3) contacting the copper pregnant organic phase with an aqueous acidic stripping solution, whereby copper values are stripped from the organic phase into the aqueous acidic stripping solution;
(4) separating said aqueous acidic stripping solution from said organic phase; and
(5) recovering the copper from said aqueous acidic stripping solution;

the improvement in the process in the present invention being the use of a highly sterically hindered beta-diketone extractant.

In view thereof, the present invention also contemplates a new copper extractant, which comprises a beta-diketone copper extractant having attached to one carbonyl carbon of the beta-diketone an aryl or alkaryl group and attached to the other carbonyl carbon a neoalkyl group containing from 6 to about 16 carbon atoms, such as 1-phenyl-3-(1-neoalkyl)-1, 3-propanedione.

As indicated earlier, the present invention is useful in regard to aqueous ammoniacal solutions from a variety of sources such as those encountered in leaching of chalcocite concentrates. In such applications the copper pregnant leach solutions from which the copper is to be recovered by extraction will contain on the order of about 15–170 g/l copper and typically about 30–40 g/l copper at a pH of about 8.5 to 11. In solutions encountered from other applications, the solutions may contain copper at higher levels, on the order of 125–170 g/l, such as solutions encountered in ammoniacal copper chloride printed board etchants.

The improvement in the process comprises employing a sterically hindered beta-diketone of the formula I or II. The sterically hindered beta-diketones may be of the structure [I]:

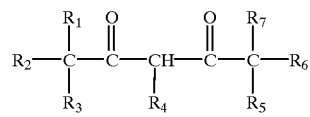

wherein $R_1$ through $R_3$ and $R_5$ through $R_7$ are the same or different, and are chosen from the group consisting of hydrogen, an aryl radical, an alkaryl radical containing from 6 to about 18 carbon atoms, and an alkyl radical containing from 1 to about 13 carbon atoms, and $R_4$ is chosen from the group consisting of H and an electron withdrawing group such as chloro, nitro and cyano with the provisos that (a) any two of $R_1$ through $R_7$ may together form a carbocyclic ring, (b) no more than three of $R_1$ through $R_7$ may be hydrogen, (c) the overall molecule contains at least 12 carbon atoms, and (d) $R_5$, $R_6$ and $R_7$ taken together comprise a mixture of isomers.

In a second embodiment of the invention, the sterically hindered beta-diketones may be of the formula [II]:

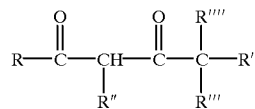

Compounds of formula II are modifications of the beta-diketones found in U.S. Pat. Nos. 4,065,502 and 4,175,012. The hindered beta-diketones of the present invention are those where R is phenyl or alkyl substituted phenyl, R' is alkyl, R" is chosen from the group consisting of H and an electron withdrawing group such as chloro, nitro and cyano and R'" and R"" are the same or different and are chosen from the group consisting of H, alkyl having from 1 to about 8 carbon atoms, and aralkyl having from 7 to about 14 carbon atoms, with the proviso that (a) no more than one of R", R'" and R"" are H and (b) the total number of carbons in all R groups is at least 11 and preferably at least 12. Preferred compounds are those in which (i) R is phenyl, R" is H, R' is propyl or isopropyl, R'" is ethyl and R"" is methyl; (ii) R is phenyl, R" is H, R' is a mixture of branched hexyl groups, R'" and R"" are methyl, and (iii) R is phenyl, R" is H, R' is a straight or branched chain alkyl group containing from 3–8 carbon atoms and R'" and R"" are methyl.

Particularly preferred beta-diketones are those prepared from condensation of acetophenone with esters such as methyl neooctanoate, methyl neononanoate and methyl neodecanoate. In relation to the diketone, the neo prefix means that the carbon next to the carbonyl carbon is completely substituted in the diketone, thus a neoalkyl group can be illustrated as

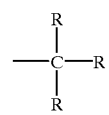

in which the R groups, which may be the same or different are all alkyl groups. Accordingly in formula II above, R', R'", and R"", which may be the same or different, are all alkyl groups containing from 1–8 carbon atoms. Generally neoalkyl groups are a mixture of isomers. The neoalkyl group in the beta-diketones of this invention will contain a total from 6 to about 16 carbon atoms. The total number of carbon atoms in the overall beta-diketone molecule will contain at least 15 carbon atoms and may preferably contain up to about 24 carbon atoms. The most preferred diketones of formula II are those where R is phenyl or alkaryl, R" is H and R', R'" and R"" are each alkyl and the total carbon atoms taken together in R', R'" and R"" contain from 5 to about 16 carbon atoms, represented by neoalkyl groups such as neohexyl, neoheptyl, neooctyl, neononyl and neodecyl. Especially preferred are those diketones where the total carbon atoms taken together in R', R'" and R"" contain from 6 to about 10 carbon atoms.

In the nomenclature using the neo prefix, a neoacid is a carboxylic acid containing a neoalkyl group. For example, neodecanoic acid, a mixture of isomers available from Exxon, is a ten-carbon carboxylic acid containing a neo-nonyl alkyl group. Similarly, neooctanoic acid is an eight-carbon carboxylic acid containing a neoheptyl alkyl group. As an example of the mixtures present in the beta-diketones of the invention, the neoheptyl group is typically a mixture of isomers in which R' is propyl or isopropyl, R'" is ethyl and R"" is methyl, and in which R' and R'" are ethyl, and R"" is methyl. Similarly, the neononyl group is typically a mixture of isomers in which R' is a mixture of branched hexyl isomers, and R'" and R"" are methyl, and in which R' is a mixture of straight chain and branched butyl and pentyl groups, R'" is a mixture of ethyl and propyl groups, and R"" is methyl, wherein the total of R', R'" and R"" taken together is eight.

The various R groups in formula I or II are preferably free from substitution and each contains less than about 20 carbon atoms.

The preferred diketone found to be particularly suitable in the past is 1-phenyl-3-isoheptyl-1,3-propanedione wherein the carbon attaching the isoheptyl group to the carbonyl group is not tertiary. However, as earlier noted, when such diketone under conditions of use is exposed to high levels of ammonia, and particularly where relatively high temperatures are encountered, such as 45 degrees Centigrade, the result is the formation of the corresponding ketimine which then results in poor stripping kinetics and may be an intermediate in a degradation pathway resulting in by-products that may contribute to very high entrainment of the aqueous phase in the loaded organic. In addition, a significant amount of ammonia is coextracted with the copper, resulting in additional costs due to ammonia loss and the corresponding acid consumption. Surprisingly, beta-diketones of formula II containing the preferred neoalkyl group not only have a much reduced tendency toward formation of ketimine degradation products, but also coextract substantially less ammonia, and retain very fast stripping kinetics, even upon prolonged exposure to ammoniacal copper solutions. The beta-diketones containing a neoalkyl group, where R', R'" and R"" are all alkyl, are preferred over beta-diketones wherein R" is H and one of R', R'" and R"" is also H, such as 1-phenyl-4-ethyl-1,3-octanedione; the latter compound has improved resistance to ketimine formation, but coextracts nearly the same amount of ammonia as does 1-phenyl-3-isoheptyl-1,3-propanedione, and gives substantially slowed stripping kinetics after prolonged exposure to ammoniacal copper solution. The carbon alpha to the carbonyl carbon must be fully substituted with alkyl groups to obtain improvement in all the above properties.

In the process of extraction a wide variety of water immiscible liquid hydrocarbon solvents can be used in the copper recovery process to form the organic phase in which the diketone extractant is dissolved. These include aliphatic and aromatic hydrocarbons such as kerosenes, benzene, toluene, xylene and the like. A choice of essentially water-immiscible hydrocarbon solvents or mixtures thereof will depend on factors, including the plant design of the solvent extraction plant, (mixer-settler units, extractors) and the like. The preferred solvents for use in the present invention are the aliphatic or aromatic hydrocarbons having flash points of 130 degrees Fahrenheit and higher, preferably at least 150 degrees and solubilities in water of less than 0.1% by weight. The solvents are essentially chemically inert. Representative commercially available solvents are Chevron™ ion exchange solvent (available from Standard Oil of California) having a flash point of 195 degrees Fahrenheit; Escaid™ 100 and 110 (available from Exxon—Europe) having a flash point of 180 degrees Fahrenheit; Norpar™ 12 (available from Exxon—USA) with a flash point of 160 degrees Fahrenheit; Conoco™ C1214 (available from Conoco) with a flash point of 160 degrees Fahrenheit; and Aromatic 150 (an aromatic kerosene available from Exxon—USA having a flash point of 150 degrees Fahrenheit), and other various kerosenes and petroleum fractions available from other oil companies, such as the ORFORM™ SX series of solvent extraction diluents (available from Phillips 66: SX 1, 7, 11, and 12 each having a Flash Point above 150° F. varying up to 215° F.); and the ESCAID™ series of hydrocarbon diluents (available from Exxon: 100, 110, 115, 120, 200 and 300, each having a Flash Point above 150° F.); and EXXOC™ D80 solvent (also available from Exxon and having a Flash Point above 150° F.).

In the extraction process, the organic solvent solutions may contain the beta-diketone in an amount approaching 100% solids, but typically the diketone will be employed in an amount of about 20–30% by weight.

In the process, the volume ratios of organic to aqueous (O:A) phase will vary widely since the contacting of any quantity of the diketone organic solution with the copper containing aqueous ammoniacal solution will result in the extraction of copper values into the organic phase. For commercial practicality however, the organic:aqueous phase ratios for extraction are preferably in the range of about 50:1 to 1:50. It is desirable to maintain an effective O:A ratio of about 1:1 in the mixer unit by recycle of one of the streams. In the stripping step, the organic:aqueous stripping medium phase will preferably be in the range of about 1:4 to 20:1. For practical purposes, the extracting and stripping are normally conducted at ambient temperatures and pressure although higher and lower temperatures and pressures are entirely operable. While the entire operation can be carried out as a batch operation, most advantageously the process is carried out continuously with the various streams or solutions being recycled to the various operations in the process for recovery of the copper, including the leaching, extraction and the stripping steps.

In the extraction process the extractant reagent should be soluble in the organic water-immiscible solvent. In general the diketones of the present invention will be soluble to such an extent and amount described above. If necessary or desirable to promote specific desired properties of extraction, solubility modifiers generally known in the art may be employed. Such modifiers include long chain (6–30 carbon aliphatic alcohols or esters such as n-hexanol, n-2-ethylhexanol, isodecanol, isohexadecanol, 2-(1,3,3 trimethylbutyl)-5,7,7-trimethyl octanol and 2,2,4-trimethyl-1,3-pentanediol mono- or di-isobutyrate, long chain phenols, such as heptylphenol, octylphenol, nonylphenol and dodecylphenol; and organo phosphorous compounds such as tri-lower alkyl (4–8 carbon atom) phosphates especially tributyl phosphate and tri-(2-ethylhexyl) phosphate. Where indicated to be desirable, kinetic additives may also be employed. It is preferred to avoid solubility modifiers.

The present invention also contemplates the use of a catalytic amount of an oxime, in which case the oxime functions as a kinetic additive, in combination with the sterically hindered diketones of the present invention, preferably an hydroxy, aryl oxime. By catalytic amount as employed herein, is meant a small amount of oxime in relation to the amount of diketone, preferably from about 0.5 to about 5 mole % of oxime relative to the beta-diketone. Such amounts of oxime are particularly effective in accelerating the rate of copper stripping from the organic phase.

The beta-diketones of this invention are also effective as co-extractants for copper from ammoniacal solutions along with strong extractants, such as oximes, a combination similar to that described in U.S. Pat. No. 4,350,661 noted earlier above. In such a case, the mixture of diketone and oxime in the extraction reagent will comprise about 5–30 volume percent of the oxime strong reagent and about 10–60 volume percent of the weaker beta-diketone.

The oxime compounds which are to be employed in catalytic amounts along with the sterically hindered beta-diketones, or may be co-extractants with the beta-diketones are certain oximes such as described in U.S. Pat. No. 4,563,256. Such oximes, which may be employed are those generally conforming to the formula:

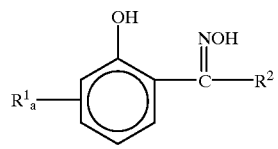

where $R^1$ is a saturated aliphatic group of 1–25 carbon atoms or an ethylenically unsaturated group of 3–25 carbon atoms or $OR^3$, where $R^3$ is a saturated or ethylenically unsaturated group as defined above, a is an integer of 0, 1, 2, 3 or 4 and $R^2$ is H, or a saturated or ethylenically unsaturated group as defined above, with the proviso that the total number of carbon atoms in $R^1$ and $R^2$ is from 3–25, or is phenyl or $R^4$ substituted phenyl where $R^4$ is a saturated or ethylenically unsaturated group as defined above, which may be the same or different from $R^1$. Illustrative of some of the oxime compounds are 5-heptyl salicylaldoxime, 5-octyl salicylaldoxime, 5-nonyl salicylaldoxime, 5-dodecyl salicylaldoxime, 5-nonyl-2-hydroxyacetophenone oxime, 5-dodecyl- 2-hydroxyacetophenone oxime, 2-hydroxy-5-nonyl benzophenone oxime and 2-hydroxy-5-dodecyl benzophenone oxime. While it may be preferred that a single oxime compound be employed along with the beta-diketone, mixtures of oximes may be employed to meet particular system requirements.

In the stripping step, a sulfuric acid solution containing about 60–180 g/l sulfuric acid is the preferred stripping agent as it permits the subsequent recovery of the copper by conventional recovery steps either in the form of copper sulphate crystals or by electrowinning to cathode copper. Other mineral acids may be used such as hydrochloric or nitric; however, such may require other recovery methods or specialized handling equipment.

The following example is illustrative of the procedure by which an alkyl or aralkyl substituent may be introduced into the beta-diketones of Mackay U.S. Pat. Nos. 4,065,502 and 4,175,012, such as 1-phenyl-3-isoheptyl-1,3-propanedione.

A mixture of 55.2 g anhydrous potassium carbonate, 1.6 g tetrabutylammonium fluoride, 24.8 g 1-phenyl-3-isoheptyl-1,3-propanedione and 150 ml. toluene were stirred and heated to reflux for 2 hours with a Dean-Stark trap under a nitrogen atmosphere. The mixture was cooled to room temperature, 7.0 ml methyl iodide was added and the mixture was heated with stirring to 50 degrees Centigrade overnight. The product was diluted with toluene and water, and the organic phase washed with water, and stripped under reduced pressure. The residue was distilled in a Kugelrohr apparatus at 100–110 degrees Centigrade at 0.3 mm Hg to give 25.6 g distillate. The distillate was purified on a silica gel column and redistilled in a Kugelrohr apparatus to give 16.4 g of 1-phenyl-2-methyl-3-isoheptyl-1,3-propanedione. Employing the same procedure using benzyl iodide will provide the corresponding 1-phenyl-2-benzyl-3-isoheptyl-1, 3-propanedione.

Other hindered beta-diketones may be prepared by the method of Example A of U.S. Pat. No. 4,065,502. Alternatively, a preferred method of preparation is the condensation of acetophenone with an appropriate methyl ester in an aromatic hydrocarbon solvent using excess sodium hydride as base. Thus, methyl neooctanoate is condensed with acetophenone to give 1-phenyl-3-neoheptyl-1, 3-propanedione, and methyl 2,2-dimethyl octanoate is condensed with acetophenone to give 1-phenyl-4,4-dimethyl-1, 3-decanedione, in which the product is a mixture of branched chain isomers.

It was found that a highly hindered beta-diketone prepared from the condensation of acetophenone with methyl neooctanoate (a) gives good stability in the presence of ammoniacal copper solutions; (b) retains its very fast stripping kinetics even under conditions of aging and (c) co-extracts only a fraction of the amount of ammonia as does 1-phenyl-3-isoheptyl-1,3-proponedione, a diketone employed in the past described in U.S. Pat. No. 4,065,502; while (d) maintaining good extraction strength. By comparison, 1-phenyl-4-ethyl-1,3-propanedione, a compound of Formula II wherein R" and R'" are both H, gives good stability in the presence of ammoniacal copper solutions, but co-extracts nearly the same amount of ammonia as does 1-phenyl-3-isoheptyl-1,3-propanedione, and has only moderately faster stripping kinetics. This can be further seen by means of the following experimental data.

EXAMPLE 1

Preparation of 1-Phenyl-3-Neoheptyl-1,3 Propanedione

A 500 mL, 4 neck round bottom flask equipped with mechanical stirring, a nitrogen inlet, a thermometer, a condenser and an addition funnel was charged with 60% sodium hydride in mineral oil (20.5 g. 0.51 mol), methyl neooctanoate (92.3 g., 0.58 mol, prepared from neo-octanoic acid, a product of Exxon), and xylene (42.8 g.). The mixture was heated to reflux (135° C.), and then a solution of acetophenone (32.4 g. 0.27 mol) in xylene (19.1 g.) was added over 1.25 h. The mixture was kept at reflux for an additional 1 h. After cooling to room temperature, the reaction was quenched by the careful addition of methanol (20 mL), and then acidified with 150 g/L sulfuric acid (180 mL). After separation of layers, the organic phase was washed with water (2×100 mL) and brine (100 mL). After drying by passing through anhydrous sodium sulfate, the solution was concentrated in vacuo at 70° C. down to 12 mbar to yield an orange liquid containing product in a crude yield of 63%. Vacuum distillation (200 mtorr) through a 15 cm Vigreux column yielded the product in the heart cut: 1-phenyl-3-neoheptyl-1,3-propanedione (X) (37.2 g., 96% pure, 0.14 mol; 53% yield; bp: 94–135° C.). Dypnone, the self-condensation product of acetophenone was undetectable in the product.

By substituting methyl 2-ethylhexanoate for the methyl neo-octanoate in the above procedure, 1-phenyl-4-ethyl-1,3-octanedione (Y) was also prepared.

1-phenyl-3-isoheptyl-1,3-propanedione (Z) derived from condensation of acetophenone with methyl isooctanoate, was prepared the method of Example A of U.S. Pat. No. 4,065,502. In (Z), carbon 4, adjacent to the carbonyl carbon, bears two hydrogens and one alkyl group. In (Y), that carbon bears one hydrogen and two alkyl groups. In (X), that carbon bears no hydrogens and three alkyl groups. According to Exxon the supplier of neooctanoic acid used in the preparation of (X), this material is a mixture of isomers, the most predominant of which contains a methyl, an ethyl and a propyl substituent on the carbon alpha to the carboxylic acid.

EXAMPLE 2

Copper Extraction Testing

An organic phase was prepared by dissolving the beta-diketone in Conoco 170E (a kerosene available from Conoco, Inc.) to give a 0.95M solution. One volume of organic phase was shaken two minutes with an aqueous feed solution containing 30 g/l Cu, 1.5 g/l Zn, 23 g/l ammonium sulphate, and 56 g/l ammonia, and the organic phase was filtered and analyzed for copper. A portion of the filtered organic was shaken two minutes with an equal volume of sodium phthalate buffer solution containing 0.1M of titratable acidity; the filtered aqueous phase was analyzed for copper, and was titrated for remaining acidity to allow calculation of ammonia transferred from the organic phase to the aqueous buffer phase. Finally, a portion of the loaded and filtered organic was shaken for two minutes with an equal volume of an aqueous solution containing 30 g/l Cu, 30 g/l ammonium sulfate and 30 g/l ammonia; the resulting maximum loaded organic phase was filtered and analyzed for copper. Results for the compounds (X), (Y) and (Z) are given in the following table.

|   | Response | (X) | (Y) | (Z) |
|---|---|---|---|---|
| A. | One Contact Loading, g/l Cu | 20.8 | 22.4 | 23.5 |
| B. | Maximum Loading, g/l Cu | 27.3 | 27.8 | 30.03 |
| C. | % of Mx. Ld. (A/B) | 76% | 81% | 78% |
| D. | Loaded $NH_3$, mM | 7.6 | 16.5 | 19 |
| E. | Mole % $NH_3$ rel. to Cu | 2.3% | 4.7% | 5.1% |

The value for the one contact loading as a percentage of the maximum loading capacity is a measure of extraction strength of the beta-diketone. The fact that the values in row C are about the same indicates that the increase in steric hindrance did not weaken the ability to extract copper. However, the loaded ammonia for compound (X) is substantially lower than either compounds (Y) or (Z), indicating that the most highly hindered beta-diketone significantly reduces the co-extraction of ammonia with copper.

EXAMPLE 3

Effect of Aging with Ammoniacal Copper

A solution of beta-diketone in Conoco 170E was mixed in a round bottomed flask with an equal volume of aqueous solution containing 30 g/l Cu, 20 g/l ammonium sulfate and 44 g/l ammonia for six days at 45° C. The organic phase was then separated, and the loaded copper stripped by contacting with successive portions of 150 g/l aqueous sulfuric acid until the organic was light yellow, and then washed twice with water and filtered. A sample of the filtered organic was analyzed by gas chromatography to detect any conversion to ketimine. The amount of ketimine is reported as a percent of the diketone present; detection limit is less than 0.01%.

| Compound | % Ketimine |
|---|---|
| X | none |
| Y | none |
| Z | 0.98% |

The data show that the tendency toward ketimine formation is strongly reduced upon increasing of steric crowding.

EXAMPLE 4

Determination of Stripping Kinetics

A 130 ml portion of filtered organic from Example 3 was loaded with copper by shaking two minutes with 115 ml of aqueous solution containing 30 g/l Cu, 1.5 g/l Zn, 23 g/l ammonium sulphate, and 56 g/l ammonia, and the resulting organic was filtered. A sample of the filtered organic was analyzed for copper. Then 100 ml of filtered organic was mixed with 100 ml of aqueous containing 35 g/l Cu and 150 g/l sulfuric acid in a 2½ inch square mixer box equipped with a 1¼ inch diameter slotted disk impeller turning at 1780 rpm. Samples of emulsion were withdrawn at specified time intervals, and the separated organic was filtered and analyzed for copper. Results are given based on the g/l Cu stripped after one minute as a percentage of the g/l Cu stripped after 15 minutes. An additional result for compound (Z) is provided in which the stripping kinetics were determined prior to aging.

| Compound | % Stripped |
|---|---|
| (X) | 100%-essentially complete in 20 seconds |
| (Y) | 88% |
| (Z) | 53% |
| (Z) | 74%-prior to aging; rate depends on time the loaded organic stands exposed to co-extracted ammonia |

The data show that, with a high degree of steric crowding, the kinetics of copper stripping is very fast, and remains fast even after aging with ammoniacal copper solution. By contrast, the less hindered compound (Z) has a stripping rate before aging which is variable, depending on how long the loaded organic stands with co-extracted ammonia, and a rate after aging which is very slow. The compound (Y) having an intermediate degree of steric hindrance gives stripping kinetics which are significantly slower than the most hindered compound (X).

These hindered beta-diketones are then employed in a process for the recovery and extraction of copper from an aqueous ammoniacal copper containing solution as described earlier above in steps (1) through (5).

What is claimed is:

1. In a process for recovery of copper from an aqueous ammoniacal solution containing copper values comprising:

(A) contacting a copper pregnant aqueous ammoniacal solution containing copper values with a water insoluble beta-diketone copper extractant dissolved in a water-immiscible organic solvent to extract copper values from said aqueous ammoniacal solution into said organic solution thereby forming a copper pregnant organic phase and a copper depleted aqueous phase;

(B) separating said aqueous phase and said organic phase;

(C) contacting the copper pregnant organic phase with an aqueous acidic stripping solution;

(D) separating said aqueous acidic stripping solution now containing the copper values from the organic phase; and (E) recovering the copper from said aqueous acidic stripping solution;

wherein the improvement comprises said water insoluble beta-diketone extractant being a highly sterically hindered beta-diketone.

2. A process as defined in claim 1 wherein the sterically hindered beta-diketone has the formula I:

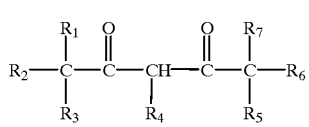

[I]

wherein $R_1$ through $R_3$ and $R_5$ through $R_7$ are the same or different, and are chosen from the group consisting of hydrogen, an aryl radical, an alkaryl radical containing from 6 to about 18 carbon atoms, and an alkyl radical containing from 1 to about 13 carbon atoms, and $R_4$ is chosen from the group consisting of H, chloro, nitro and cyano with the provisos that (a) any two of $R_1$ through $R_7$ may together form a carbocyclic ring, (b) no more than three of $R_1$ through $R_7$ may be hydrogen, and (c) the overall molecule contains at least 12 carbon atoms, and (d) $R_5$, $R_6$, $R_7$ taken together comprise a mixture of at least two isomers.

3. A process as defined in claim 1, wherein the sterically hindered beta-diketone has the formula II:

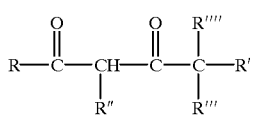

[II]

where R is phenyl or alkyl substituted phenyl, R' is alkyl, R" is chosen from the group consisting of H, chloro, nitro and cyano, and R''' and R'''' are the same or different and are chosen from the group consisting of H, alkyl having from 1 to about 8 carbon atoms, and aralkyl having from 7 to about 14 carbon atoms, with the proviso that (a) no more than one of R", R''' and R'''' are H and (b) the total number of carbons in all R groups is at least 11, and (c) R', R''' and R'''' taken together comprise a mixture of at least two isomers.

4. A process as defined in claim 3, wherein R is phenyl, R" is H, R' is propyl or isopropyl and R''' is ethyl and R'''' is methyl.

5. A process as defined in claim 3 wherein R is phenyl, R" is H, R' is branched hexyl, R''' and R'''' are methyl.

6. A process as defined in claim 3, wherein R is phenyl, R" is H, R' is a mixture of straight and branched chain alkyl groups having from 3–8 carbon atoms and R''' and R'''' are methyl.

7. A process as defined in claim 3 wherein the group

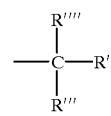

is a neoalkyl group in which R', R''' and R'''', which may be the same or different, are all alkyl groups containing from 1 to 8 carbon atoms and the total number of carbon atoms in R', R''' and R'''' is from 5 to about 16.

8. A process as defined in claim 1 wherein the diketone is a mixture of branched and straight chain isomers of 1-phenyl-4,4-dimethyl-1,3-undecanedione.

9. A process as defined in claim 1 wherein the diketone is 1-phenyl-3-neodecyl-1,3-propanedione.

10. A process as defined in claim 1 wherein the diketone is 1-phenyl-3-neoheptyl-1,3-propanedione.

11. A process as defined in claim 1 wherein the diketone is 1-phenyl-3-neohexyl-1,3-propanedione.

12. A process as defined in claim 1 wherein the diketone is 1-phenyl-3-neooctyl-1,3-propanedione.

13. A process as defined in claim 1 wherein the diketone is 1-phenyl-3-neononyl-1,3-propanedione.

14. A process as defined in claim 1, in which the extractant further comprises an hydroxy aryl oxime.

15. A process as defined in claim 14, wherein said hydroxy aryl oxime is present in a catalytic amount.

16. A process as defined in claim 14, wherein said hydroxyaryl oxime is a co-extractant with the beta-diketone.

17. A process as defined in claim 14, wherein said hydroxy aryl oxime has the formula:

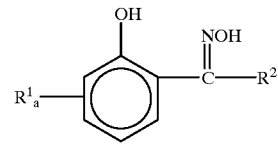

where $R^1$ is a saturated aliphatic group of 1–25 carbon atoms or an ethylenically unsaturated group of 3–25 carbon atoms or $OR^3$, where $R^3$ is a saturated or ethylenically unsaturated group as defined above, a is an integer of 0, 1, 2, 3 or 4 and $R^2$ is H, or a saturated or ethylenically unsaturated group as defined above, with the proviso that the total number of carbon atoms in $R^1$ and $R^2$ is from 3–25, or is phenyl or $R^4$ substituted phenyl where $R^4$ is a saturated or ethylenically unsaturated group as defined above, which may be the same or different from $R^1$.

18. A process as defined in claim 17, in which said hydroxy aryl oxime is selected from the group consisting of 5-heptyl salicylaldoxime, 5-octyl salicylaldoxime, 5-nonyl salicylaldoxime, 5-dodecyl salicylaldoxime, 5-nonyl-2-hydroxyacetophenone oxime, 5-dodecyl-2-hydroxyacetophenone oxime, 2-hydroxy-5-nonyl benzophenone oxime and 2-hydroxy-5-dodecyl benzophenone oxime.

19. A beta-diketone extractant compound adapted for extracting copper values from aqueous ammoniacal copper containing solutions comprising a beta-diketone compound of the formula II:

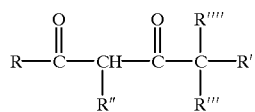 [II]

where R is phenyl or alkyl substituted phenyl, R' is alkyl, R" is selected from the group of H and an electron withdrawing group selected from the group consisting of chloro, nitro and cyano and R'" and R"" are the same or different and are chosen from the group consisting of H, alkyl having from 1 to about 8 carbon atoms, and aralkyl having from 7 to about 14 carbon atoms, with the proviso that (a) no more than one of R", R'" and R"" are H (b) the total number of carbons in all R groups is at least 11, and (c) R', R'" and R"" taken together comprise a mixture of at least two isomers.

20. A beta-diketone compound as defined in claim 19, wherein R is phenyl, R" is H, R' is propyl or isopropyl and R'" is ethyl and R"" is methyl.

21. A beta-diketone compound as defined in claim 19, wherein R is phenyl, R" is H, R' is branched hexyl and R'" and R"" are methyl.

22. A beta-diketone compound as defined in claim 19, wherein R is phenyl, R" is H, R' is a branched chain alkyl group having from 3–8 carbon atoms and R'" and R"" are methyl.

23. A beta-diketone compound as defined in claim 19 wherein the group

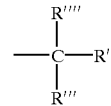

is a neoalkyl group in which R', R'" and R"", which may be the same or different, are all alkyl groups containing from 1–8 carbon atoms and the total number of carbon atoms in R', R'" and R"" is from 5 to about 16.

24. A mixture of isomers of 1-phenyl-4,4-dimethyl-1,3-undecanedione.

25. 1-phenyl-3-neoheptyl-1,3-propanedione.

26. 1-phenyl-3-neohexyl-1,3-propanedione.

27. 1-phenyl-3-neooctyl-1,3-propanedione.

28. 1-phenyl-3-neononyl-1,3-propanedione.

* * * * *